United States Patent [19]

Cohen et al.

[11] 4,191,842

[45] Mar. 4, 1980

[54] PROTECTED ALCOHOLS

[75] Inventors: Noal Cohen, Montclair; Gabriel Saucy, Essex Fells, both of N.J.

[73] Assignee: Hoffmann-La Roche Inc., Nutley, N.J.

[21] Appl. No.: 4,102

[22] Filed: Jan. 17, 1979

Related U.S. Application Data

[60] Division of Ser. No. 802,747, Jun. 2, 1977, Pat. No. 4,151,205, which is a division of Ser. No. 639,011, Dec. 9, 1975, Pat. No. 4,051,153, which is a continuation-in-part of Ser. No. 544,163, Jan. 27, 1975, Pat. No. 4,000,161.

[51] Int. Cl.² ............................................. C07C 43/04
[52] U.S. Cl. .......................... 568/662; 260/345.9 R; 260/448.2 B; 568/675; 568/678; 568/594; 568/596

[58] Field of Search ............... 568/662, 675, 678, 594, 568/596; 260/345.9 R, 448.2 B

[56] References Cited

U.S. PATENT DOCUMENTS

| 2,875,251 | 2/1959 | Rigterink | 568/662 |
| 3,381,039 | 4/1968 | Marbet | 568/594 |

OTHER PUBLICATIONS

Schneiderman et al., Chem. Absts., 64, 8691(a) (1966).

*Primary Examiner*—Bernard Helfin
*Assistant Examiner*—G. T. Breitenstein
*Attorney, Agent, or Firm*—Jon S. Saxe; Bernard S. Leon; William H. Epstein

[57] ABSTRACT

A synthesis of vitamin E in racemic or optically active forms from methacrylein or beta-hydroxyisobutyric acid including intermediates in this synthesis.

3 Claims, No Drawings

PROTECTED ALCOHOLS

CROSS REFERENCE TO RELATED APPLICATIONS

This application is a divisional application of Ser. No. 802,747 filed June 2, 1977—Cohen et al., now U.S. Pat. No. 4,151,205, which in turn is a divisional application of Ser. No. 639,011 filed Dec. 9, 1975—Cohen et al, now U.S. Pat. No. 4,051,153. Said application Ser. No. 639,011 is a continuation-in-part application of U.S. patent application Ser. No. 544,163, Cohen and Saucy, filed Jan. 27, 1975 now U.S. Pat. No. 4,000,161.

This application is also related to U.S. patent application Ser. No. 417,465, filed Nov. 19, 1973, Scott, Parrish and Saucy now U.S. Pat. No. 3,947,473, which is incorporated herein by reference.

BACKGROUND OF THE INVENTION

In the past, optically active alpha-tocooherol and derivatives thereof which are the 2R',4'R,8'R isomers of compounds of the formula:

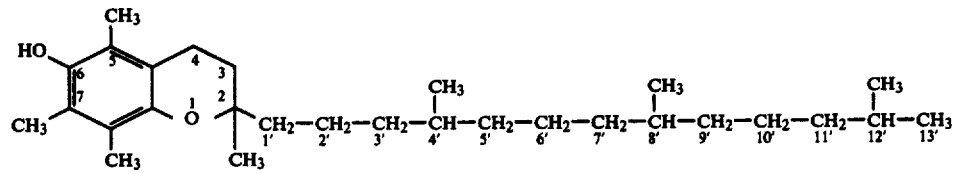

have been prepared through isolation from natural sources such as vegetable oil. This procedure suffers from many drawbacks due to the fact that the tocopherol content of these oils is very small. Therefore, a great amount of oil must be processed in order to isolate a small amount of natural tocopherol. Additionally, the process whereby various tocopherols are isolated from vegetable oil is extremely cumbersome.

In U.S. patent application Ser. No. 417,465, filed Nov. 19, 1973, Scott et al., vitamin E active compounds have been synthesized by utilizing a compound of the formula:

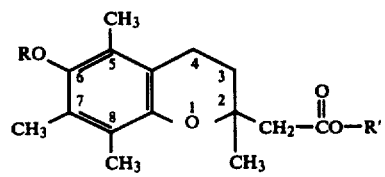

wherein
  R forms with its attached oxygen moiety an ether protecting group removable by hydrogenolysis or acid catalyzed cleavage; and
  R' is lower alkyl; and a compound of the formula:

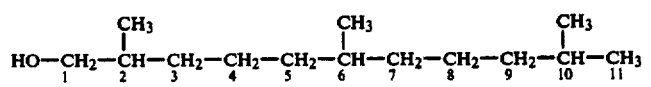

The compound of formula II can be a racemate or a 2R or 2S isomer, depending upon the desired isomeric form of the compound of formula I. (Please note, the compound of the formula VII in U.S. patent application Ser. No. 417,465, filed Nov. 19, 1973).

The compound of formula III can also be a racemate or various 2 and 5, R and S isomers. (Please note compound XLIV in U.S. patent application Ser. No. 417,465, filed Nov. 19, 1973). Where the compound of the formula III has a 2R, 6R configuration, i.e., a compound of the formula:

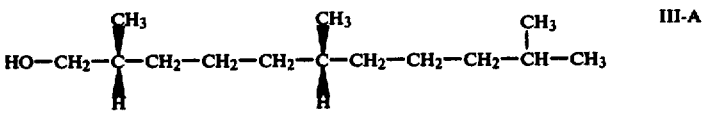

then natural α-tocopherol is produced when the compound of the formula III-A and the 2S isomer of the compound of formula II are utilized.

In accordance with this process, it has been desired to provide a simple and economic method for preparing the compound of formula III and III-A, natural vitamin E and isomers derived therefrom from relatively cheap and economic starting materials.

SUMMARY OF THE INVENTION

In accordance with this invention, it has been discovered that the compound of formula III or its optically active 2R,6R isomer as well as other isomers can be prepared from the compound of the formula

wherein
  R is as above;
  X is a halogen; or a compound of the formula:

via the condensation of a compound of the formula:

wherein R and X are as above, with a compound of the formula:

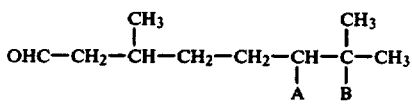

wherein A and B are hydrogen or taken together form a carbon to carbon bond; or via the condensation of a compound of the formula:

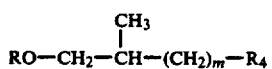

with a compound of the formula:

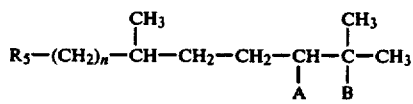

wherein
A and B are as above;
one of $R_4$ or $R_5$ is —$CH_2MgX$ and the other is —$CH_2OR_6$;
X is as above;
—$OR_6$ is a leaving group;
and m and n are integers from 0 to 1 with the proviso that the sum of m and n is equal to 1.

In accordance with this invention, a method is provided for utilizing the compound of formula II and the compound of formula III to produce the compound of formula I in any isomeric form, among which are the following:
2RS, 4'RS, 8'RS;
2R, 4'RS, 8'RS;
2S, 4'RS, 8'RS;
2RS, 4'R, 8'R;
2S, 4'R, 8'R;
2R, 4'R, 8'R;
2RS, 4'RS, 8'R;
2S, 4'RS, 8'R;
2R, 4'RS, 8'R;
2RS, 4'R, 8'RS;
2R, 4'R, 8'RS; and
2S, 4'R, 8'RS.

Hence, the process of this invention provides a means for synthesizing the compound of formula I in all of its various isomeric forms.

DETAILED DESCRIPTION OF THE INVENTION

The numbering of the claims in formula I, II, III and III-A, above, is shown for the purpose of convenience.

As used throughout this application, the term "lower alkyl" comprehends both straight and branched chain saturated hydrocarbon groups containing from 1 to 7 carbon atoms such as methyl, ethyl, propyl, isopropyl, etc. As used throughout this application, the term "halogen" includes all four halogens, such as bromine, chlorine, fluorine and iodine. The term "alkali metal" includes sodium, potassium, lithium, etc.

In the pictorial representation of the compounds given throughout this application, a ( ▼ ) tapered line indicates a substituent which is pointed out of the plane of the paper towards the reader.

The term "lower alkoxy" as used throughout the specification denotes lower alkoxy groups containing from 1 to 7 carbon atoms such as methoxy, ethoxy, propoxy, isopropoxy, etc. The term "lower alkanoyl" as used throughout this specification denotes lower alkanoyl groups containing from 2 to 6 carbon atoms such as acetyl or propionyl.

As also used herein, the term "aryl" signifies mononuclear aromatic hydrocarbon groups such as phenyl, tolyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be unsubstituted or substituted with one or more of the aforementioned groups. The preferred aryl groups are the substituted and unsubstituted mononuclear aryl groups, particularly phenyl. The term "aryl lower alkyl" comprehends groups wherein aryl and lower alkyl are as defined above, particularly benzyl. The term "aroic acid" comprehends acids wherein the aryl group is defined as above. The preferred aroic acid is benzoic acid.

As still further used herein, the term "ester protecting group removable by hydrolysis" comprehends any conventional organic acid protecting group which can be removed by hydrolysis. Any conventional ester that can be hydrolyzed to yield the acid can be utilized as the protecting group. Exemplary esters useful for this purpose are the lower alkyl esters, particularly methyl, and the aryl esters particularly phenyl, and the aryl lower alkyl esters, particularly benzyl ester. The alcohols utilized to form the hydrolyzable ester protecting group are lower alkanols, aryl lower alkanols and reactive derivatives thereof.

The term "ether protecting group removable by hydrogenolysis or acid catalyzed cleavage" designates any ether which, upon acid catalyzed cleavage or hydrogenolysis yields the hydroxy group. A suitable ether protecting group is, for example, the tetrahydropyranyl ether or 4-methyl-5,6-dihydro-2H-pyranyl ether. Others are arylmethyl ethers such as benzyl, benzhydryl or trityl ethers or alpha-lower alkoxy lower alkyl ether, for example, methoxymethyl or allylic ethers, or trialkyl silyl ethers such as trimethyl silyl ether or dimethyl-tert.-butyl silyl ethers. Other ethers which are preferred are tertiary butyl ethers.

The preferred ethers which are removed by acid catalyzed cleavage are t-butyl and tetrahydropyranyl. Acid catalyzed cleavage is carried out by treatment with a strong organic or inorganic acid. Among the preferred inorganic acids are the mineral acids such as sulfuric acid, hydrohalic acid, etc. Among the preferred organic acids are lower alkanoic acids such as acetic acid, trifluoroacetic acid, etc. and arylsulfonic acids such as para-toluene sulfonic acid, etc. The acid catalyzed cleavage can be carried out in an aqueous medium or in an organic solvent medium. Where an organic acid is utilized, the organic acid can be the solvent medium. In the case of t-butyl, an organic acid is generally utilized with the acid forming the solvent medium. In the case of tetrahydropyranyl ethers, the cleavage is generally carried out in an aqueous medium. In carrying out this reaction, temperature and pressure are not critical and this reaction can be carried out at room temperature and atmospheric pressure.

The preferred ethers which are removable by hydrogenolysis are the aryl methyl ethers such as benzyl or substituted benzyl ethers. The hydrogenolysis can be carried out by hydrogenation in the presence of a suitable hydrogenation catalyst. Any conventional method of hydrogenation can be utilized in carrying out this procedure. Any conventional hydrogenation catalyst such as palladium or platinum can be utilized.

In accordance with the invention, the compound of formula III is produced through the condensation of a compound of the formula VI with the compound of the formula VII. Condensation of the compound of formula VI above with the compound of the formula VII produces a compound of the formula:

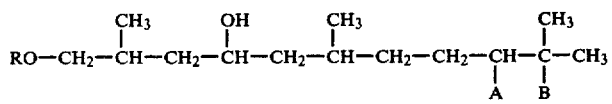

wherein R, A and B are as above.

The compound of formula X can be converted to the compound of formula III via the following intermediates:

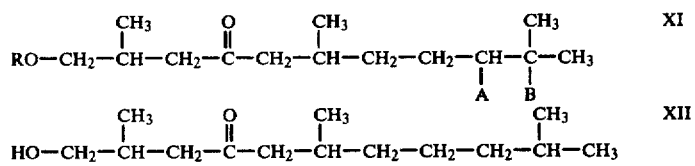

wherein R, A and B are as above.

The condensation of the compound of formula VI with a compound of formula VII is carried out via a Grignard reaction. Any of the conditions conventional in Grignard reactions can be utilized to carry out this condensation. This condensation produces the compound of the formula X. The compound of formula X can be converted to the compound of formula XI by oxidation. Any conventional method of oxidizing a secondary alcohol to a ketone can be utilized in carrying out this method. Among the preferred oxidizing agents are the chromate oxidizing agents such as chromium trioxide-pyridine complex (Collins reagent), chromium trioxide dispersed in a carrier such as graphite (Lalancette reagent), chromium trioxide in pyridine (Sarrett reagent) and chromic acid (Jones reagent). Any of the conditions conventional in utilizing these oxidizing agents can be utilized in the conversion of a compound of a formula X to a compound of the formula XI.

The compound of formula XI, where R forms an ether protecting group removable by hydrogenolysis is converted to the compound of the formula XII by hydrogenation. Any conventional method of hydrogenation can be utilized in carrying out this invention. In accordance with the preferred embodiment of this invention, hydrogenation is carried out in the presence of a noble metal hydrogenation catalyst. Any conventional noble metal hydrogenation catalyst can be utilized to carry out this procedure. Among the conventional noble metal hydrogenation catalysts are included palladium and platinum. Another metal hydrogenation catalyst which can be utilized in this reaction is Raney nickel. The hydrogenation catalyst may be present in this reaction in the combination with a conventional support. Any of the conventional supports such as carbon, charcoal, etc. may be utilized in combination with the aforementioned metals to provide a catalyst system for use in this reaction step. In carrying out this hydrogenation reaction, temperature and pressure are not critical and this reaction can take place at room temperature and atmospheric pressure. On the other hand, elevated temperatures and pressures can be utilized. This hydrogenation step removes the ether protecting group "R" where the ether protecting group is removable by hydrogenolysis. On the other hand, where R in the compound of formula XI forms an ether removable by acid catalyzed cleavage, hydrogenation of the compound of formula XI will reduce any double bond formed by A and B but will not affect the ether group. Removal of this ether group in the compound of formula XI is effected by acid catalyzed cleavage such as described hereinbefore.

The compound of formula XII is converted to the compound of formula III utilizing any conventional method of reducing a ketone group to the corresponding —$CH_2$—group. Among the preferred methods of reduction is the Wolff-Kischner reduction. In carrying out this reduction, any of the conditions conventional in Wolff-Kischner reduction can be utilized. Among the preferred methods is to subject the compound of the formula XII to hydrazine in the presence of a base such as an alkali metal hydroxide. Generally, this reaction is carried out in a temperature of from 150° C. to 250° C.

The compound of formula VII is a known compound. The compound of formula VI where R forms an ether which is removable by hydrogenolysis such as benzyl is prepared from a compound of formula V via the following intermediates:

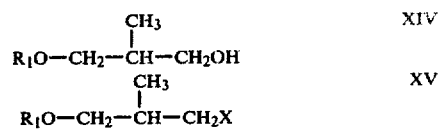

wherein R and X are as above and $R_1$ taken together with its attached oxygen atom forms an ether protecting group removable by hydrogenolysis such as benzyl ether.

The compound of formula V is converted to the compound of formula XIV by reacting the compound of formula V with a compound of the formula:

$R_1OH$ wherein $R_1$ is as above.

This reaction is carried out in the presence of an inorganic base such as sodium hydroxide and an alkali metal borohydride reducing agent. In carrying out this reaction, any conventional alkali metal borohydride reducing agent such as sodium borohydride can be utilized. The temperature and pressure utilized in this reaction are not critical and this reaction can be carried out at room temperature and atmospheric pressure. On the other hand, elevated or reduced temperatures can be utilized. Generally, it is preferred to carry out this reaction at a temperature of from about −25° C. to 50° C.

The compound of formula XIV is converted to the compound of formula XV by treating the compound of formula XIV with a halogenating agent. Any of the conditions conventional in halogenating an alcohol can be utilized to carry out this reaction. Among the conventional halogenating agents which can be utilized are included phosphorus tribromide, triphenyl phosphine dibromide and thionyl chloride. Any of the conditions conventional in utilizing these halogenating agents can be utilized to convert the compound of the formula XIV to the compound of the formula XV.

The compound of formula XV is converted to the Grignard reagent, i.e,, a compound of the formula VI, utilizing conventional procedures for preparing Grignard reagents. For example, the Grignard reagent is prepared by reacting the halide of formula XV with magnesium in an ether reaction medium, for example, ethyl ether or tetrahydrofuran at elevated temperatures, generally in the range of from about 40° C. to 80° C.

On the other hand, the compound of formula XIV where R₁ taken together with its attached oxygen moiety forms an ether protecting group removable by acid catalyzed cleavage such as t-butyl and tetrahydropranyl can be prepared from a compound of the formula:

via the following intermediate:

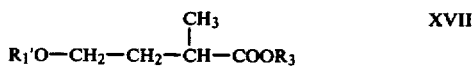

wherein
R₃ taken together with its attached oxygen moiety forms a hydrolyzable ester group and;
R₁' taken together with its attached oxygen atoms forms an ether protecting group removable by acid catalyzed cleavage.

The hydroxy acid of the compound of the formula XVI, in the first step of this synthesis, is esterified and etherified so that both its free hydroxy groups are protected. In this step, the free —CH₂OH group is etherified to form an ether removably by acid catalyzed cleavage while the

group is esterfied to form a hydrolyzable ester. The ether and the ester group can be formed separately. On the other hand, a hydrolyzable ether and hydrolyzable ester may be formed in one step by reacting the hydroxy acid with isobutylene in the presence of an inorganic acid and boron trifluoride etherate. This reaction can be carried out at low temperatures such as −10° C. to −100° C. By this reaction, the acid group is esterified and the hydroxy group is etherified with a tertiary butyl group. Among the preferred ether groups are included t-butyl and tetrahydropyranyl. In forming this ether, any of the conventional conditions utilized in reacting hydroxy groups with activated alcohol derivatives can be utilized. On the other hand, the acid group of the hydroxy acid of formula XVI can be esterified by reacting the acid with a reactive alcohol derivative. Conditions conventional in forming esters can be utilized to carry out this reaction. Among the preferred esters are those where the R₃ forms a lower alkyl group.

The compound of the formula XVII is converted to the compound of formula XIV by treating the compound of formula XVII with an aluminum hydride reducing agent. Any of the conventional aluminum hydride reducing agents such as lithium aluminum hydride or diisobutyl aluminum hydride can be utilized in this reaction. Among the other preferred reducing agents are the alkyl aluminum hydrides reducing agents such as diisoamyl aluminum hydride, etc. as well as sodium dihydrobis[2-methoxyethoxy]-aluminum hydride. The reduction with an aluminum hydride reducing agent is carried out in an inert organic solvent medium. Any conventional inert organic solvent medium can be utilized for carrying out this reaction. Among the preferred inert organic solvents are included pentane, dioxane, diethyl ether, hexane, toluene, benzene or xylene. Generally, temperatures of from about −120° C. to about 30° C. are utilized in carrying out this reduction reaction.

Where it is desired to produce the compound of formula III with a 2R configuration, the starting material of formula XVI having an S configuration is utilized. This compound has the formula:

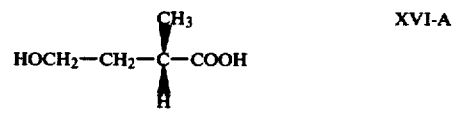

The configuration about the asymmetric carbon atom in this starting material is maintained throughout its synthesis to the compound of formula VI and the conversion of the compound of formula VI to a compound of formula III. In this manner, the final product of formula III has a 2R configuration. If the starting material of formula XVI is racemic about its asymmetric carbon atom, then the final product of formula III has a 2RS configuration. The same is true with regard to the starting material of formula V and the products produced thereby.

On the other hand, if the compound of formula VII which has the formula:

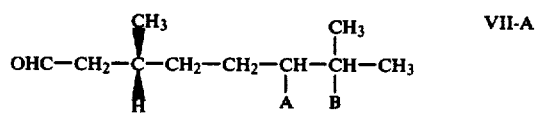

wherein A and B are above; is utilized as a starting material, the compound of formula III produced thereby has a 6R configuration. If the compound of formula VII has a 2RS configuration about the asymmetric carbon atoms, the compound of formula III which is produced thereby as a 6RS configuration.

When the compound of formula VIII is condensed with the compound of the formula IX, a compound of the formula:

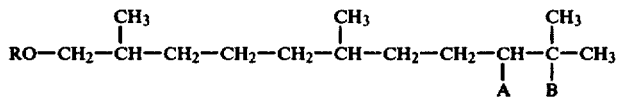

is produced; wherein R, A and B are as above.

This compound can be converted to a compound of formula III or a compound of the formula:

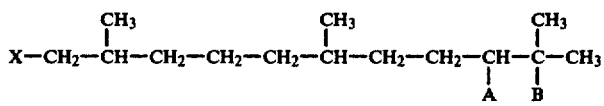

wherein A, B and X are as above.

In the compounds of formulae VIII or IX, $R_6$ can be any conventional leaving group. Among the preferred leaving groups formed by —$OR_6$ are alkyl sulfonyloxy such as methylsulfonyloxy, aryl sulfonyloxy, such as p-toluenesulfonyloxy, naphthyl-sulfonyloxy, etc.

The compound of formula VIII and IX are reacted to form the compound of formula XX in the presence of a di(alkali metal) tetrahalocuprate utilizing the procedure disclosed by Fouquet and Schlosser on pages 82 and 83 of *Angew Chem Internat. Edit.* Vol. 13 (1974). In the procedure disclosed by Fouquet and Schlosser, carbon to carbon linkage of hydrocarbons is carried out through the reaction of a magnesium halide with a sulfonyl ester. In accordance with this invention, it has been discovered that this reaction can be carried out with an ether or chroman functional group so that either the magnesium halide or sulfonyl ester can carry these functional groups. In accordance with this invention, it has been discovered that the ether or chroman groups do not interfere with the reaction. In this reaction, any conventional di(alkali metal) tetrahalocuprate can be utilized with dilithium tetrachlorocuprate being preferred. Generally, this reaction is is carried out in the presence of an ether solvent. Any conventional inert organic ether solvent can be utilized. Among the preferred solvents are included tetrahydrofuran, dioxane, diethyl ether, dimethoxyethane, diglyme, etc.

The compound of formula XX can be converted to the compound of formula III by either hydrogenation and/or acid catalyzed cleavage. Where hydrogenation is utilized and A and B form a double bond and the ether group is removable by hydrogenolysis, hydrogenation both reduces the double bond and cleaves the ether protecting group to form the compound of formula III. Where, in the compound of formula XX, A and B form a carbon to carbon bond and -OR forms an ether removable by acid catalyzed cleavage, hydrogenation only reduces the double bond. Hydrogenation can be carried out in the same manner as described hereinbefore in connection with the hydrogenation of a compound of the formula XI to form a compound of the formula XII. The acid catalyzed cleavage can be carried out as described hereinbefore. The compound of formula III is converted to the compound of formula XXI where A and B are hydrogen by halogenation as described hereinbefore with regard to the conversion of a compound of the formula XIV to a compound of the formula XV.

On the other hand, the compound of formula XX where —OR forms an ether group removable by acid catalyzed cleavage can be directly converted to the compound of formula XXI in one step, without the necessity for forming the intermediate of the formula III. This reaction is carried out by treating the compound of formula XX with a hydrohalic acid in an aqueous medium. Any conventional hydrohalic acid such as hydrochloric acid, hydrogen bromide, etc. can be utilized in carrying out this reaction. Generally this reaction is carried out in an aqueous medium at the reflux temperature of the medium. In general, temperatures from about 80° C. to 120° C. are utilized.

The compound of formula VIII wherein m is 0 and $R_4$ is —$CH_2OR_6$, i.e., the compound of the formula:

wherein R and $R_6$ are as above; can be prepared from the compound of formula XIV by converting the free hydroxy group in the compound of formula XIV to a leaving group. Any conventional method of converting a hydroxy group to a leaving group can be utilized. Among the preferred methods is to react the compound of formula XIV with an aryl sulfonyl halide such as napthylsulfonyl halide, p-toluene sulfonyl halide, etc. or a lower alkyl sulfonyl halide as methylsulfonyl halide in the presence of an organic amine base such as pyridine, triethyl amine, etc.

Where the absolute configuration of the asymmetric carbon atom in the compound of formula VIII is S when m=0 and R when m=1, this configuration is maintained throughout its conversion into a compound of formula III having a 2R configuration. If the compound of the formula VIII is racemic, the conversion of the compound of formula VIII to a compound of formula III produces the compound of formula III which is racemic about the 2-carbon atom.

Where $R_5$ in the compound of formula IX is —$CH_2OR_6$ and n is 1, i.e., a compound of the formula:

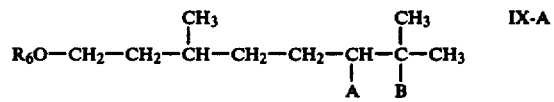

wherein $R_6$, A and B are as above is obtained.

This compound can be prepared from a known compound of the formula:

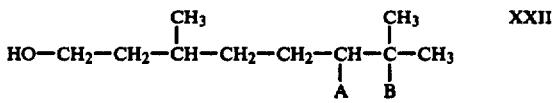

wherein A and B are as above in the same manner as described in connection with the conversion of a compound of the formula XIV to a compound of the formula VIII-A.

Where $R_5$ in the compound of formula IX is —$CH_2MgX$ and n is 1, i.e., a compound of the formula:

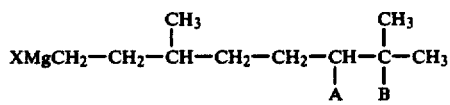

wherein X, A and B are as above is produced. This compound can be prepared from the compound of formula XXII by halogenation in the manner described hereinbefore in connection with the conversion of a compound of the formula XIV to a compound of the formula XV. The halogenation of a compound of the formula XXII produces a compound of the formula

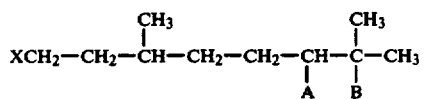

wherein X, A and B are as above. The compound of formula XXIII is converted to a compound of the formula IX-B by forming the Grignard salt in the same manner as described in connection with the formation of a compound of the formula VI from a compound of the formula XV.

Where it is desired to produce the compound of formula III with a 6R configuration, the compound of formula XXII is utilized which has a R configuration about its asymmetric carbon atom. On the other hand, where it is desired to produce the compound of formula III with a RS configuration about the 6 position, a compound of formula XXII is utilized which is racemic about the 6-carbon atom.

In accordance with another embodiment of this invention, the compound of formula VII where A and B are hydrogen can be prepared from the compound of formula IV. Where the compound of formula VII is prepared from a compound of formula IV, the following intermediates are formed:

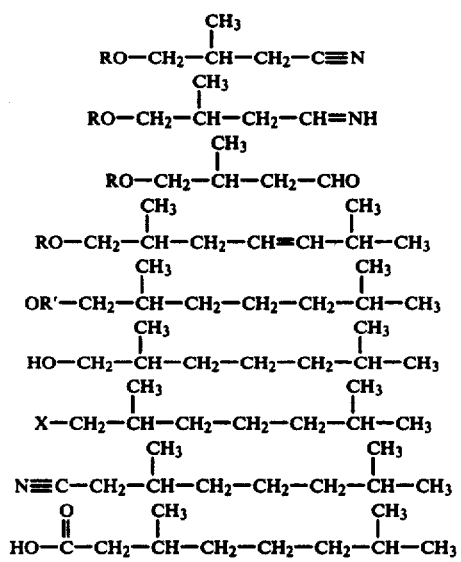

wherein
X and R are as above; and

R', taken together with its attached oxygen atom forms an ether protecting group removable by acid catalyzed cleavage.

In this synthesis of the compound of formula VII, the compound of formula IV is first treated with an alkali metal cyanide. In this manner, the compound of formula XXV is formed. This reaction is carried out by conventional procedures utilizing an aqueous lower alkanol solvent as the reaction medium. In carrying out this reaction, temperatures of from 50° C. to 100° C. are generally utilized.

In the next step, the compound of formula XXV is converted to the compound of formula XXVI by treatment with an alkali metal aluminum hydride reducing agent such as diisobutyl aluminum hydride. Among the preferred reducing agents are the alkyl aluminum hydride reducing agents such as diisobutyl aluminum hydride, diisoamyl aluminum hydride, etc. The reduction with an aluminum hydride reducing agent is carried out in an inert organic solvent medium. Any conventional inert organic solvent medium can be utilized for carrying out this reaction. Among the preferred inert organic solvents are included pentane, dioxane, diethyl ether, hexane, toluene, benzene or xylene. Generally, temperatures of from about −120° C. to about 30° C. are utilized in carrying out this reduction reaction.

The compound of formula XXVI is converted to the compound of formula XXVII by acid hydrolysis in an aqueous medium. Where R in the compound of formula XXVI forms an ether group removable by hydrogenolysis, any strong inorganic acid such as sulfuric acid, hydrochloric acid, etc. can be utilized. In this case, any conventional method of acid hydrolysis can be utilized. On the other hand, where R forms an ether protecting group removable by acid catalyzed cleavage, weak acids which provide a pH to the aqueous medium of from 4–5 can be utilized. The preferred weak acid is ammonium chloride. In this reaction, temperature and pressure are not critical and the hydrolysis can be carried out at room temperature and atmospheric pressure. If desired, higher or lower temperatures can be utilized.

The compound of formula XXVII is converted to a compound of formula XXVIII by reacting the compound of formula XXVII with a phosphorane of the formula:

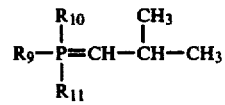

wherein $R_9$, $R_{10}$ and $R_{11}$ are aryl via a Wittig type reaction. Any of the conditions conventional in Wittig type condensations can be utilized in carrying out this reaction. Where R forms an ether group removable by hydrogenolysis, the compound of formula XXVIII is converted to a compound of formula XXX by hydrogenation. This hydrogenation is carried out in the same manner as described in connection with the hydrogenation of a compound of the formula XI to a compound of the formula XII. On the other hand, where R in the compound of formula XXVIII forms an ether group removable by acid catalyzed cleavage, hydrogenation converts the compound of formula XXVIII to a compound of formula XXIX. The compound of formula XXIX is converted to the compound of formula XXX by acid catalyzed cleavage in the manner described hereinbefore.

The compound of formula XXIX can also be prepared from the reaction of a compound of the formula

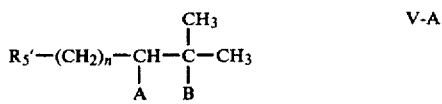

with a compound of the formula VIII illustrated as follows:

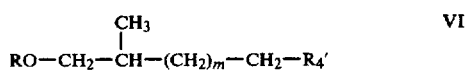

wherein one of $R_4'$ or $R_5'$ is —MgX and the other is —$OR_6$, m, n, R, $R_6$, A and B are as above; with the proviso that the sum of m and n is equal to 1 to produce a compound of the formula

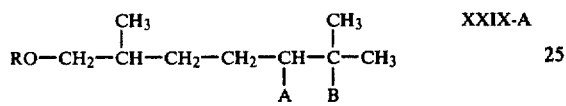

wherein R, A and B are as above.

If in the compound of formula XXIX-A, R forms an ether group removable by acid catalyzed cleavage and A and B form a double bond, this compound can be hydrogenated to form a compound of formula XXIX. On the other hand, when R in the compound of formula XXIX-A forms an ether protecting group removable by hydrogenolysis, and A and B are hydrogen or form a double bond, this compound can be hydrogenated to form the compound of formula XXX.

The reaction of the compound of formulas V-A and VIII is carried out in the same manner described hereinbefore with regard to the reaction of a compound of the formula VIII with a compound of formula IX. Where the absolute configuration of the asymmetric carbon atoms in the compound of formula VIII is S when m is 0, or R when m is 1, conversion of the compound of formula VIII into the compound of formula XIX results in the compound of formula XIX having an R configuration about its asymmetric carbon atoms. Where the compound of formula VIII is racemic, the compound of formula XXIX will also be racemic.

The compound of formula XXX is converted to the compound of formula XXX-A by halogenation. This halogenation is carried out in the same manner as described hereinbefore in connection with the conversion of a compound of the formula XIV to a compound of the formula XV. The compound of formula XXX-A is converted to the compound of formula XXXI by reacting the compound of formula XXX-A with an alkali metal cyanide. This reaction is carried out in the same manner as described in connection with the conversion of a compound of the formula IV to a compound of the formula XXV. The compound of the formula XXXI is converted to the compound of the formula XXXII by hydrolysis with an alkali metal hydroxide. Any conventional alkali metal hydroxide can be utilized. Generally this reaction is carried out in an aqueous medium. In carrying out this reaction, temperature and pressure are not critical and this reaction can be carried out at from 30° C. to 150° C. The compound of formula XXXII can be converted into the compound of formula XXII where A and B are hydrogen by reduction of the acid to an alcohol. Any conventional method of reducing an acid to an alcohol can be utilized in this reaction. This reduction can be carried out utilizing an alkali metal aluminum hydride reducing agent as described in connection with the conversion of a compound of the formula XVII to a compound of the formula XIV. The compound of formula XXII where A and B are hydrogen can be converted to the compound of formula VII where A and B are hydrogen by oxidation. Any conventional oxidizing agent capable of oxidizing an alcohol to an aldehyde can be utilized to affect this conversion.

The compound of formula XXV can be utilized to prepare the compound of formula VIII where $R_4$ is —$CH_2OR_6$ and m is 1 via the following interrmediates:

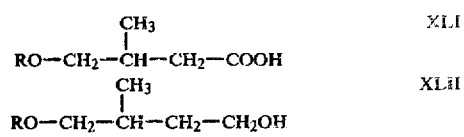

wherein R is as above.

In the first step of this reaction, the compound of formula XXV is hydrolyzed utilizing the same conditions as described hereinbefore in connection with the conversion of a compound of the formula XXVI to a compound of the formula XXVII. This hydrolysis of the compound of the formula XXV produces a compound of the formula XLI which is reduced in the manner described hereinbefore in connection with the conversion of a compound of the formula XXXII to a compound of the formula XXII. This reduction, which is carried out with an alkali metal aluminum hydride reducing agent, produces a compound of the formula XLII. The hydroxy group in the compound of formula XLII is then converted to a leaving group, i.e., the compound of formula VIII where $R_4$ is —$CH_2OR_6$ and m is 1 in the manner hereinbefore described in connection with the formation of a compound of the formula VIII-A.

When $R_5$ in the compound of formula IX is —$CH_2MgX$ and n is 0, a compound of the formula

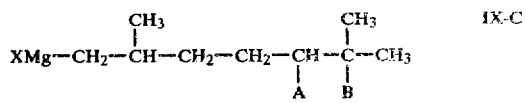

wherein A, B and X are as above is produced. This compound can be prepared from a compound of formula XXIX-A where RO- forms an ether protecting group removable by acid catalyzed cleavage. In the first step this ether group in the compound of formula XXIX-A is cleaved by acid catalyzed cleavage to form the corresponding hydroxy compound. This hydroxy compound is converted to the compound of formula IX-C in the same manner as described in connection with the formation of a compound of the formula VI from the hydroxy compound of the formula XIV.

When $R_5$ in the compound of formula IX is —$OR_6$ and n is 0, a compound of the formula

IX-D

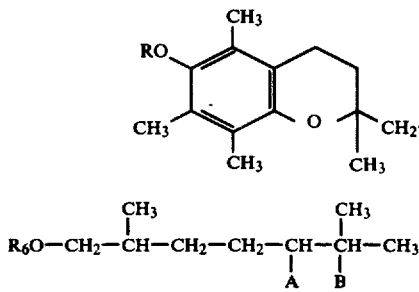

$$R_6O-CH_2-\underset{A}{\overset{CH_3}{\underset{|}{CH}}}-CH_2-CH_2-\underset{B}{\overset{CH_3}{\underset{|}{CH}}}-CH-CH_3$$

wherein $R_6$, A and B are as above is produced. This compound can be formed from the hydroxy compound produced when the compound of formula XXIX-A where —OR forms an acid catalyzed ether group is subjected to acid catalysis. This hydroxy compound is converted to the compound of formula IX-D in the same manner as described in connection with the conversion of a compound of the formula XIV to a compound of the formula VIII-A.

The compound of formula VIII where m is 1 and $R_5$ is —$CH_2MgX$ can be prepared from the compound of the formula XLII by halogenation to produce a compound of the formula $$RO-CH_2-\overset{CH_3}{\underset{|}{CH}}-CH_2-CH_2X \qquad \text{XLIII}$$

wherein R and X are as above followed by forming the Grignard salt in the same manner as described in connection with the formation of a compound of the formula VI from a compound of the formula XV. The halogenation is carried out in the same manner as described in connection with the conversion of a compound of the formula XIV to a compound of the formula XV.

The compound of the formula VIII where m is 1 and $R_5$ is —$CH_2OR_6$ can be prepared from the compound of the formula XLII in the same manner as described in connection with the conversion of a compound of the formula XIV to a compound of the formula VIII-A.

In accordance with this invention, the compound of formula I is prepared by condensing a compound of the formula:

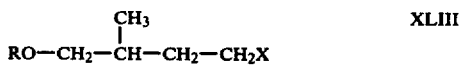

wherein X is as above; with a compound of the formula:

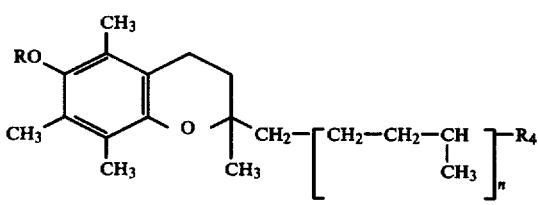

wherein R, $R_4$, $R_5$, m and n are as above with the proviso that when n is 1, R is $R_1$; via an intermediate of the formula:

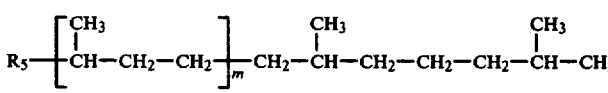

wherein R is as above.

The compound of formula LI when n is 0, i.e., a compound of the formula:

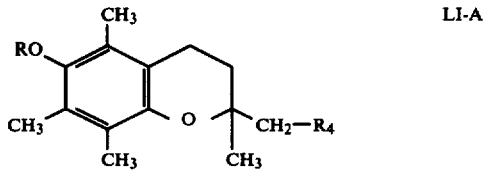

wherein $R_4$ and R are as above; is prepared from the compound of formula II via the following intermediate:

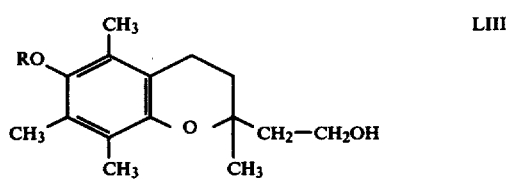

wherein R is as above.

The compound of formula II is converted to the compound of formula LIII by reduction with an alkali metal aluminum hydride reducing agent. This reduction is carried out in the same manner as described hereinbefore in connection with the reduction of the compound of the formula XVII to form the compound of the formula XIV. Any of the conventional alkali metal aluminum hydride reducing agents such as described hereinbefore can be utilized in carrying out this conversion. The compound of formula LIII is converted to the compound of the formula LI where n is 0 and $R_4$ is —$CH_2OR_6$ in the same manner as described in connection with the conversion of a compound of the formula XIV to a compound of the formula VIII-A. Any conventional method of converting a hydroxy group to a leaving group can be utilized. Among the preferred methods is to react the compound of formula LIII with an aryl sulfonyl halide such as naphthyl sulfonyl halide or p-toluenesulfonyl halide or a lower alkyl sulfonyl halide such as methyl sulfonyl halide.

The compound of formula LIII can be converted to the compound of formula LI where $R_4$ is —$CH_2MgX$ and n is 0 by halogenating the compound of formula LI and forming the Grignard salt in the same manner as described in connection with the formation of a compound of the formula IX-B from a compound of the formula XXII.

The compound of the formula LI where n is 1, i.e., a compound of the formula:

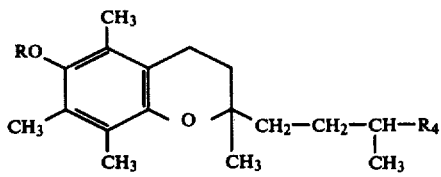

LI-B wherein $R_1$ and $R_4$ are as above; is prepared by first condensing the compound of the formula LI-A with a compound of the formula VIII wherein m is 0 and R is $R_1'$ to produce a compound of the formula:

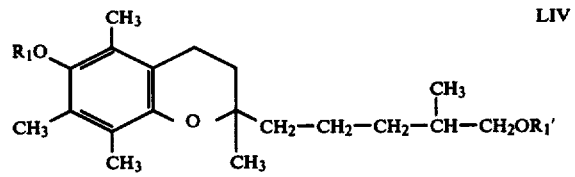

LIV wherein $R_1$ and $R_1'$ are as above. This condensation is carried out in the same manner as described in connection with the reaction of a compound of the formula VIII and IX to form the compound of formula XX.

The compound of formula LIV is converted to the compound of the formula:

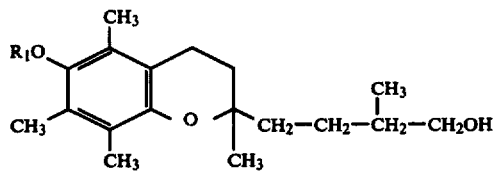

LIV wherein $R_1$ is as above; by acid catalyzed cleavage as described hereinbefore. The compound of formula LIV is converted to the compound of formula LI-B wherein $R_4$ is $-CH_2MgX$ by halogenation and formation of the Grignard salt as described in connection with the formation of a compound of the formula IX-B to form a compound of the formula XXII.

The compound of the formula LIV is converted to the compound of the formula LI-B where $R_4$ is $-CH_2OR_6$ in the same manner as described in connection with the conversion of a compound of the formula XIV to a compound of the formula VIII-A.

The compound of formula L where m is 1 is prepared from the compound of formula XXI. The compound of formula XXI where A and B form a carbon to carbon bond can be converted to a compound of formula XXI where A and B are hydrogen by hydrogenation in the manner described hereinbefore.

The compound of formula XXI where A and B are hydrogen can be converted to a compound of formula L where m is 1 and $R_4$ is $-CH_2MgX$ by forming a Grignard salt. Any conventional method of forming a Grignard salt can be utilized in forming this compound of formula L. This conversion can be carried out in the same manner as described in connection with the conversion of a compound of formula XV to a compound of formula VI.

The compound of formula L where m is 0 is the compound of formula IX where n is 1 and A and B are hydrogen.

The condensation of a compound of the formula L with a compound of the formula LI is carried out in the same manner as that described in connection with the condensation of a compound of the formula VIII with a compound of the formula IX. This reaction produces the compound of the formula LII. Depending upon whether RO in the compound of formula LII forms an ether group removable by acid catalyzed cleavage or hydrogenolysis, the compound of formula LII is converted to the compound of formula I by either hydrogenolysis or acid catalyzed cleavage. Hydrogenolysis and acid catalyzed cleavage can be carried out in the manner described hereinbefore.

Where the compound of formula II has a 2S configuation, a compound of the formula I having a 2R configuration is produced. On the other hand, where the compound of formula II has a 2R configuration, the compound of formula I having a 2S configuration is produced. Furthermore, where the compound of formula II has a 2RS configuration, the compound of formula I having a 2RS configuration is produced.

Where the compound of formula III has a 2RS, 6RS configuration, the compound of formula I is produced with 4'RS, 8'RS configuration. Furthermore, where the compound of formula III has a 2R,6R configuration, the compound of formula I produced thereby has a 4'R, 8'R configuration. On the other hand, where the compound of the formula III has a 2S, 2'RS, 6R configuration, the compound of the formula I produced thereby has a 4'RS, 8'R configuration. Also, if the compound of formula III has a 2R, 6RS configuration, the compound of formula I produced thereby has a 4'R, 8'RS configuration.

The following examples are illustrative but not limitative of the invention. All temperatures are in degrees centigrade and the ether is diethyl ether. The 5% palladium on carbon designates a catalyst containing 5% by weight palladium on 95% by weight carbon. The term "THF" refers to tetrahydrofuran.

EXAMPLE 1

(S)-(+)-tert. Butyl 3-tert. butoxy-2-methylpropionate

A solution of 8.7 g. of S-(+)-β-hydroxyisobutyric acid in 140 ml. of $CH_2Cl_2$ was stirred and cooled to $-72°$ C. (dry ice-acetone bath) whereupon 70 ml. of liquid isobutylene was added rapidly. To the resulting mixture was added with stirring at $-72°$ C., a solution of 1.6 ml. of phosphoric acid (prepared by dissolving 5 g. of phosphorus pentoxide in 11 ml. of 85% by weight phosphoric acid) in 10 ml. of $CH_2Cl_2$, dropwise followed by 3.5 ml. of boron trifluoride etherate also dropwise. The resulting mixture was stirred at $-72°$ C. for 2 hours and at $0°-5°$ C. (ice bath) for 20 hours then treated with 300 g. of ice-water followed by a solution of 19 g. of $NaHCO_3$ in 200 ml. of water. The $CH_2Cl_2$ layer was removed and the aqueous layer was extracted twice with $CH_2Cl_2$. The combined organic extracts were washed twice with brine then dried ($MgSO_4$), filtered and concentrated in vacuo giving 23.3 g. of crude product as a yellow oil. This material was chromatographed on 200 g. of silica gel. Elution with 19:1 parts by volume and 9:1 parts by volume hexane-ether gave the desired product which was distilled yielding 12.7 g. (79%) of the ether ester (S)-(+)-tert. butyl 3-tert. butoxy-2- methylpropionate as a colorless liquid, b.p. 99° C. (22 mm Hg.); [α]$^{25}$D+19.52° (c 4.25, CH$_3$OH).

EXAMPLE 2

(R)-(+)-3-tert. Butoxy-2-methyl-1-propanol

A slurry of 11.2 g. (0.295 mole) of lithium aluminum hydride in 470 ml. of anhydrous diethyl ether was stirred with ice bath cooling while a solution of 31.9 g. (0.1475 mole) of (S)-(+)-tert. butyl 3-tert. butoxy-2-methylpropionate in 470 ml. of anhydrous ether was added dropwise over 70 minutes. After stirring at 0°-5° C. for 0.5 hour and at room temperature for 3 hours, the reaction mixture was again chilled and cautiously decomposed by the dropwise addition of 22.4 ml. of water and 17.9 ml. of 10% by weight aqueous NaOH solution. The resulting mixture was stirred at room temperature for 16 hours then the solids were filtered and washed thoroughly with ether. The filtrate and washes were combined and concentrated at aspirator pressure. Distillation of the residue afforded 19.3 g. (89.3%) of (R)-(+)-3-tert. butoxy-2-methyl-1-propanol as a colorless liquid, b.p. 76° C. (13 mm Hg.); [α]$^{25}$D+0.47° (c 4.06, CH$_3$OH).

EXAMPLE 3

(S)-(+)-3-tert. Butoxy-2-methyl-1-bromopropane

A solution of 25.8 g. (0.176 mole) of (R)-(+)-3-tert. butoxy-2-methyl-1-propanol and 50.5 g. (0.193 mole) of triphenylphosphine in 105 ml. of CH$_2$Cl$_2$ was stirred while 32.8 g. (0.184 mole) of N-bromosuccinimide was added in portions, keeping the temperature below 30° C. with occasional ice bath cooling. The resulting solution was stirred at room temperature for one hour then most of the solvent was distilled under a water aspirator pressure using a Vigreaux column. The product was distilled from the residue using a short distilling head giving 0.7 g. of forerun b.p. 58°-62° C. (23 mm Hg) and then the main fraction (31.1 g.) b.p. 62°-69° C. (14-18 mm Hg). The total distillate (31.8 g.) was chromatographed on 450 g. of silica gel. Elution with 19:1 parts by volume and 9:1 parts by volume hexane-ether yielded the pure (S)-(+)-3-tert. butoxy-2-methyl-1-bromopropane which was distilled giving 26 g. (70.6%) of colorless liquid, b.p. 71° C. (16 mm Hg); [α]$^{25}$D+23.32° (c 4.23, C$_6$H$_6$).

EXAMPLE 4

Mixture of (2R,4R,6R)- and (2R,4S,6R)-1-tert. Butoxy-2,6,10-trimethylundecan-4-ol To a stirred mixture of 1.01 g. (0.0421 mole) of powdered magnesium in 10 ml. of anhydrous tetrahydrofuran was added a crystal of iodine and a few drops of a solution of 7.35 g. (0.0351 mole) of (S)-(+)-3-tert. butoxy-2-methyl-1-bromopropane in 14 ml. of dry tetrahydrofuran. The mixture was brought to reflux and after reaction had begun, the remainder of the bromide solution was added dropwise to the refluxing mixture. After the addition was complete, the reaction mixture was stirred at reflux for an additional one hour then cooled to 0°-5° C. whereupon a solution of 5.48 g. (0.0351 mole) of optically pure R-(+)-dihydrocitronellal in 27 ml. of dry tetrahydrofuran was added dropwise to the solution of S-3 tert. butoxy-2-methyl-propylmagnesium bromide keeping the temperature at 4°-8° C. The reaction mixture was stirred for 3 hours at room temperature then treated with water and saturated aqueous NH$_4$Cl solution. The product (9.5 g.) was isolated by ether extraction using the general work up procedure described in Example 1 and then chromatographed on 450 g. of silica gel. Elution with 4:1 parts by volume and 2:1 parts by volume hexane-ether gave a mixture of (2R,4R,6R)- and (2R,4S,6R)-1-tert. butoxy-2,6,10-trimethylundecan-4-ol which was distilled under high vacuum as a colorless oil, b.p. 98°-114° C., (0.05 mm Hg.).

EXAMPLE 5

(2R,6R)-(+)-1-tert-Butoxy-2,6,10-trimethylundecan-4-one

A solution of 6 g. (0.021 mole) of the mixture of (2R,4R,6R)- and (2R,4S,6R)-1-tert. butoxy-2,6,10-trimethylundecan-4-ol in 90 ml. of acetone was stirred with ice bath cooling while 6 ml. (0.024 mole) of 4 M aqueous H$_2$CrO$_4$ solution was added dropwise, over a 12 minute period. The reaction mixture was treated with 12% aqueous NaHSO$_3$ solution and water and the product was isolated by ether extraction in the manner described in Example 1 giving 5.9 g. of a colorless oil. This material was chromatographed on 300 g. of silica gel. Elution with 19:1 parts by volume hexane-ether gave the (2R,6R)-(+)-1-tert. butoxy-2,6,10-trimethylundecan-4-one which was distilled under high vacuum yielding 5.0 g. (83.8%) of a colorless oil, b.p. 87°-95° C. (0.03 mm Hg); [α]$^{25}$ D +6.62° (c 2.03, CH$_3$OH).

EXAMPLE 6

(2R,6R)-1-Hydroxy-2,6,10-trimethylundecan-4-one

A 5 g. (0.0176 mole) sample of (2R,6R)-(+)-1-tert. butoxy-2,6,10-trimethylundecan-4-one was stirred at 0° C. while 62.5 ml. of cold trifluoroacetic was added dropwise over 0.5 hour. The resulting solution was kept at 0° C. for 4.5 hour then poured onto a mixture of ice and excess 10% aqueous NaOH. The product was isolated by ether extraction by the procedure of Example 1 giving 3.98 g. (99%) of (2R,6R)-1-hydroxy-2,6,10-trimethylundecan-4-one as a pale yellow oil.

EXAMPLE 7

(2R,6R)-(+)-2,6,10-Trimethylundecan-1-ol

A mixture of 3.98 g. (0.0174 mole) of (2R,6R)-1-hydroxy-2,6,10-trimethylundecan-4-one, 108 ml. of diethylene glycol, 25 g. of KOH and 43.5 ml. of hydrazine hydrate was stirred and heated until distillation began. Distillation was then continued until the internal temperature of the reaction mixture reached 195° C. then the mixture was maintained at reflux for 4 hours. After cooling, the resulting mixture was treated with ice and 3 N aqueous HCl and worked-up by ether extraction in the manner of Example 1 giving 2.9 g. of a pale yellow oil. This material was chromatographed on 180 g. of silica gel. Elution with 4:1 parts by volume hexane-ether yielded (2R,6R)-(+)-2,6,10-trimethylundecan-1-ol which was evaporatively distilled affording 2.22 g. of a colorless oil, b.p. 90°-105° C. (bath temperature) (0.2 mm Hg.); [α]$^{25}$ D+9.44° (c 2.04, hexane).

EXAMPLE 8

(R)-(+)-3,7-Dimethyl-1-octyl p-toluenesulfonate

To a solution of 14.2 g. (0.09 mole) of optically pure R-(+)-dihydrocitronellol in 250 ml. of anhydrous pyridine at 0° C. was added 34.4 g. (0.18 mole) of p-toluenesulfonyl chloride in portions. The resulting mixture was kept at 0° C. for 22 hours then treated with ice-water. The precipitated oil was extracted with ether and the ether extracts were combined, washed with cold 1 N aqueous HCl, saturated aqueous NaHCO$_3$ and water then dried over anhydrous K$_2$CO$_3$-Na$_2$SO$_4$. After filtration and removal of the solvent in vacuo, there was obtained 27.9 g. (99.3%) of (R)-(+)-3,7-dimethyl-1-octyl p-toluenesulfonate as a yellow oil.

EXAMPLE 9

(S)-(+)-3-tert. Butoxy-2-methyl-1-propyl p-toluenesulfonate

Using the procedure of Example 8, (R)-(+)-3-tert. butoxy-2-methyl-1-propanol was converted into the (S)-(+)-3-tert. butoxy-2-methyl-1-propyl p-toluenesulfonate in quantitative yield. (S)-(+)-3-tert. butoxy-2-methyl-1-propyl p-toluenesulfonate was obtained as a colorless liquid; $[\alpha]^{25}$ D+8.18° (c 4.22, C$_6$H$_6$).

EXAMPLE 10

(R)-(−)-1-Bromo-3,7-dimethyloctane

To a solution of 10 g. (0.0633 mole) of optically pure R-(+)-dihydrocitronellol and 18.1 g. (0.069 mole) of triphenylphosphine in 38 ml. of CH$_2$Cl$_2$ was added 11.8 g. (0.0663 mole) of N-bromosuccinimide in portions, with occasional ice-bath cooling, keeping the temperature below 30° C. After stirring at room temperature for one hour, the solvent was removed in vacuo (aspirator). The residue was treated with hexane and filtered and the solids were washed thoroughly with hexane. Concentration of the combined hexane extracts left 15 g. of crude bromide which was chromatographed on 300 g. of silica gel. Elution with hexane and 49:1 parts by volume hexane-ether gave the pure bromide which was distilled affording 11.5 g. (82.3%) of (R)-(−)-1-bromo-3,7-dimethyloctane as a colorless liquid, b.p. 105°-108° C. (18 mm Hg); $[\alpha]^{25}$ D−5.7° (neat).

EXAMPLE 11

(2R,6R)-(+)-1-tert. Butoxy-2,6,10-trimethylundecane

A solution of (S)-3-tert. butoxy-2-methyl-1-propylmagnesium bromide was prepared from 3.34 g. (0.016 mole) of the S-(+)-3-tert. butoxy-2-methyl-1-bromopropane and 0.42 g. (0.0176 mole) of magnesium powder in a total of 14 ml. of dry tetrahydrofuran as described in Example 4. To a stirring solution of 2 g. (6.4 moles) of (R)-(+)-3,7-dimethyl-1-octyl p-toluenesulfonate in 6 ml. of dry tetrahydrofuran cooled to −78° C. was added 7 ml. (~8 mmoles) of this Grignard solution dropwise followed by 0.33 ml. of a 0.1 M Li$_2$CuCl$_4$ solution in dry tetrahydrofuran. The resulting mixture was stirred at −78° C. for 10 minutes then in an ice bath (0°-5° C.) for 2 hours and finally at room temperature for 16.5 hours. The reaction mixture was treated with 1 N aqueous H$_2$SO$_4$ and the product was isolated by extraction with ether in the manner of Example 1. Chromatography of the crude product (1.7 g.) on silica gel (50 parts) afforded pure (2R,6R)-(+)-1-tert. butoxy-2,6,10-trimethylundecane (eluted with 49:1 parts by volume hexane-ether). Evaporative distillation gave 1.19 g. (68.8%) of (2R,6R)-(+)-1 tert. butoxy-2,6,10-trimethylundecane as a colorless oil, b.p. 75°-80° C. (bath temperature) (0.05 mm Hg.); $[\alpha]^{25}$ D+1.29° (c 2.01, hexane).

EXAMPLE 12

(2R,6R)-(+)-1-tert. Butoxy-2,6,10-trimethylundecane

A mixture of 2.33 g. (0.097 mole) of powdered magnesium and a few iodine crystals in 23 ml. of dry tetrahydrofuran was stirred at reflux temperature while a solution of 17.9 g. (0.08 mole) of (R)-(−)-1-bromo-3,7-dimethyloctane in 51 ml. of dry tetrahydrofuran was added dropwise over 1 hour. The mixture was stirred at reflux for an additional 1 hour then cooled to room temperature. To a solution of 19.5 g. (0.065 mole) of (S)-(+)-3-tert. butoxy-2-methyl-1-propyl p-toluenesulfonate in 56 ml. of dry tetrahydrofuran, stirring at −78° C. was added the R-3,7-dimethyl-1-octyl magnesium bromide solution dropwise, followed by 3.3 ml. of a 0.1 M Li$_2$CuCl$_4$ solution in dry tetrahydrofuran. The resulting mixture was stirred at −78° C. for 10 minutes, for 2 hours at 0°-5° C. (ice bath) and finally for 18 hours at room temperature. At the end of this time, the reaction mixture was treated with 1 N aqueous H$_2$SO$_4$ and work up was carried out by extraction with ether in the manner of Example 1. The crude product was chromatographed on 450 g. of silica gel. Elution with 19:1 parts by volume hexane-ether gave the desired product which was distilled under high vacuum yielding 12.5 g. of (2R,6R)-(+)-1-tert. butoxy-2,6,10-trimethylundecane as a colorless oil, b.p. 91°-95° C. (0.3 mm Hg); $[\alpha]^{25}$ D+0.94° (c 2.01, hexane).

EXAMPLE 13

(2R,6R)-(+)-2,6,10-Trimethylundecan-1-ol

A 16.9 g. (0.0626 mole) of (2R,6R)-(+)-1-tert. butoxy-2,6,10-trimethylundecane was treated dropwise with cold trifluoroacetic acid (226 ml.) at 0° C. The resulting solution was kept at 0° C. for 4 hours then concentrated at water aspirator pressure. To the residue was added 400 ml. of 5% methanolic NaOH solution. After stirring at room temperature for 15 minutes, the alkaline mixture was diluted with water and extracted with ether. The crude product (13.5 g.) isolated from the ether extracts in the manner of Example 1 was chromatographed on 500 g. of silica gel. The alcohol was eluted with 4:1 parts by volume hexane-ether and distilled under high vacuum giving 12.2 g. (91%) of colorless oil, b.p. 96°-99° C. (0.4 mm Hg); $[\alpha]^{25}$ D+9.13° (c 2.17, hexane).

EXAMPLE 14

(2R,6R)-(−)-1-Bromo-2,6,10-trimethylundecane 12.1 g. (0.0565 mole) of (2R,6R)-(+)-2,6,10-trimethylundecan-1-ol was treated with N-bromosuccinimide (10.65 g.; 0.0598 mole) and triphenylphosphine (16.5 g.; 0.063 mole) in methylene chloride (40 ml.) using the procedure described in Example 10. After purification by column chromatography and distillation, there was obtained 13.7 g. (88.4%) of (2R,6R)-(−)-1-bromo-2,6,10-trimethylundecane as a colorless oil, b.p. 90°-93° C. (0.4 mm Hg.); $[\alpha]^{25}$ D−1.152° (neat).

EXAMPLE 15

(2R,6R)-(−)-1-Bromo-2,6,10-trimethylundecane

A mixture of 1 g. (3.7 mmoles) of (2R,6R)-(+)-1-tert. butoxy-2,6,10-trimethylundecane and 10 ml. of 48% aqueous HBr was stirred and heated at reflux for 5.75 hours. The resulting mixture was cooled and worked up by ether extraction in the manner of Example 1 giving 0.9 g. of crude product. This material was chromatographed on 30 g. of silica gel. Elution with 49:1 parts by volume hexane-ether gave the (2R,6R)-(−)-1-bromo-2,6,10-trimethylundecane which was evaporatively distilled yielding 0.748 g. (73.4%) of a colorless oil, b.p. 83°–85° C. (bath temperature) (0.15 mm Hg).

EXAMPLE 16

(S)-(−)-6-Benzyloxy-2,5,7,8-tetramethylchroman-2-ethanol

A 70% solution of sodium bis (2-methoxyethoxy)-aluminum hydride in benzene (35 ml.) was stirred with ice bath cooling while a solution of 20.55 g. (0.0558 mole) of (S)-(−)-methyl-6-benzyloxy-2,5,7,8-tetramethylchroman-2-acetate in 50 ml. of benzene was added dropwise over 80 minutes keeping the temperature below 20° C. The resulting solution was stirred at room temperature for 2 hours then cautiously poured onto a mixture of ice and 1 N aqueous NaOH. Work-up by means of ether extraction in the manner of Example 1 afforded 19.8 g. of a viscous colorless oil. This material was triturated with petroleum ether (30°–60° C.) and the resulting solid was filtered, washed with petroleum ether and dried under high vacuum giving 14.95 g. (78.7%) of (S)-(−)-6-benzyloxy-2,5,7,8-tetramethylchroman-2-ethanol as a colorless solid, m.p. 55°–56° C.; $[\alpha]^{25}$ D −16.21° (c 2.03, CHCl$_3$).

EXAMPLE 17

(S)-(+)-6-Benzyloxy-2,5,7,8-tetramethylchroman-2-ethanol p-toluenesulfonate

Using the procedure of Example 8, the (S)-(−)-6-benzyloxy-2,5,7,8-tetramethylchroman-2-ethanol was converted into (S)-(+)-6-benzyloxy-2,5,7,8-tetramethylchroman-2-ethanol p-toluenesulfonate which was obtained in essentially quantitative yield as a pale-yellow glass; $[\alpha]^{25}$ D +8.40° (c 1.13, C$_6$H$_6$).

EXAMPLE 18

(S)-6-Benzyloxy-2,5,7,8-tetramethylchroman-2-ethanol methanesulfonate

A solution of 0.5 g. (1.47 mmoles) of (S)-(−)-6-benzyloxy-2,5,7,8-tetramethylchroman-2-ethanol and 0.25 ml. (0.37 g.; 3.2 mmoles) of methanesulfonyl chloride in 5 ml. of anhydrous pyridine was kept at 0° C. for 45 hours then poured into 100 ml. of ice-water and the resulting mixture was stirred for 15 minutes. The mixture was then extracted three times with ether and the combined ether extracts were washed with cold 1 N aqueous HCl followed by water and saturated brine. After drying and filtration, the ether extracts were concentrated in vacuo giving 0.587 g. (95.6%) of (S)-6-benzyloxy-2,5,7,8-tetramethylchroman-2-ethanol methane as a colorless solid, m.p. 81°–83° C.; $[\alpha]^{25}$ D −0.36° (c 0.82, C$_6$H$_6$).

EXAMPLE 19

(2R,4′R,8′R)-α-Tocopheryl benzyl ether

A mixture of 0.216 g. (9 mmoles) of magnesium powder and a crystal of iodine in 2.1 ml. of anhydrous tetrahydrofuran was stirred and treated with a few drops of a solution of 2.07 g. (7.5 mmoles) of (2R,6R)-(−)-1-bromo-2,6,10-trimethylundecane in 4.9 ml. of dry tetrahydrofuran. The mixture was brought to reflux and after reaction had begun, the remainder of the bromide solution was added dropwise at reflux. After the addition was complete, the mixture was stirred at reflux for an additional 1 hour then cooled to room temperature. This solution, containing (2R,6R)-2,6,10-trimethylundec-1-yl magnesium bromide was then added dropwise to a stirring mixture of (S)-6-benzyloxy-2,5,7,8-tetramethyl-chroman-2-ethanol methanesulfonate (2.4 g.; 5.7 mmoles) in 4.7 ml. of dry tetrahydrofuran, cooled to −72° C. After the addition of 0.27 ml. of 0.1 M Li$_2$CuCl$_4$ solution in tetrahydrofuran, the reaction mixture was stirred for 10 minutes at −72° C. then for 2 hours in an ice bath and finally for 24 hours at room temperature. After treatment with aqueous 1 N H$_2$SO$_4$, the mixture was worked up by ether extraction in the manner of Example 1 giving 3.6 g. of the crude product as a yellow oil. This material was chromatographed on 200 g. of silica gel. Fractions eluted with hexane gave oily material rich in the desired product. Further purification by rechromatography and by preparative thin layer chromatography yielded 0.343 g. of pure (2R,4′R,8′R)-α-tocopheryl benzyl ether as a pale yellow oil, $[\alpha]^{25}$ D +0.72° (c 1.95, C$_6$H$_6$).

EXAMPLE 20

(2R,4′R,8′R) α-Tocopheryl benzyl ether

A mixture of 0.28 g. (11.7 mmoles) of magnesium powder and a crystal of iodine in 2.8 ml. of dry tetrahydrofuran was stirred while a few drops of a solution of 2.68 g. (9.7 mmoles) of (2R,6R)-(−)-1-bromo-2,6,10-trimethylundecane in 6.1 ml. of dry tetrahydrofuran were added. The mixture was brought to reflux and after the Grignard reaction had begun, the remainder of the bromide solution was added dropwise while a gentle reflux was maintained. After the addition was complete, the reaction mixture was stirred and heated at reflux for an additional one hour and then cooled to room temperature. The supernatant solution of (2R,6R)-2,6,10-trimethylundec-1-yl magnesium bromide was then added dropwise, with stirring to a solution of 3.63 g. (7.35 mmoles) of the (S)-(+)-6-benzyloxy-2,5,7,8-tetramethyl-chroman-2-ethanol p-toluenesulfonate in 6.3 ml. of dry tetrahydrofuran, cooled to −78° C. After the addition of 0.36 ml. of 0.1 M dilithium tetrachlorocuprate solution in tetrahydrofuran, the reaction mixture was stirred for 10 minutes at −78° C., then for 2 hours at 0°–5° C. (ice-bath) and finally at room temperature for 19 hours. Treatment with 1 N aqueous H$_2$SO$_4$ was followed by work up by ether extraction in the manner of Example 1 giving 4.3 g. of crude product. This material was chromatographed on 200 g. of silica gel. Elution with 19:1 parts by volume hexane-ether afforded 3.55 g. (93%) of (2R,4′R,8′R)-α-tocopheryl benzyl ether as a viscous, colorless oil.

EXAMPLE 21

(2R,4′R,8′R)-α-Tocopherol

A solution of the benzyl ether in Example 20 (3.55 g.; 6.83 mmoles) in 63 ml. of ethyl acetate was stirred in an atmosphere of hydrogen in the presence of 1.77 g. of 5% palladium on carbon catalyst. After hydrogen uptake ceased, the catalyst was filtered and the filtrate was concentrated in vacuo yielding 2.90 g. of (2R,4′R,8′R)-α-tocopherol as a colorless oil. The acetate derivative of this material was a colorless, viscous oil, b.p. 180°–200° C. (bath temperature) (0.0007 mm Hg.); $[\alpha]^{25}$ D +3.03° (c 5.1, ethanol).

EXAMPLE 22 rac.-1-Benzyloxy-2,6,10-trimethyl-9-undecen-4-ol

This compound was prepared starting from the rac. 3-benzyloxy-2-methyl-1-propyl bromide and racemic citronellal using the procedure described in Example 4. Rac.-1-benzyloxy-2,6,10-trimethyl-9-undecen-4-ol was obtained as a colorless oil, b.p. 145°–150° C. (bath temperature) (0.01 mm Hg.).

EXAMPLE 23 rac.-1-Benzyloxy-2,6,10-trimethyl-9-undecen-4-one

Oxidation of the rac. 1-benzyloxy-2,6,10-trimethyl-9-undecen-4-ol using the procedure described in Example 5 gave rac.-1-benzyloxy-2,6,10-trimethyl-9-undecen-4-one in 72% yield, as a colorless oil, b.p. 117°–120° C. (bath temperature) (0.02 mm Hg.).

EXAMPLE 24 rac.-1-Hydroxy-2,6,10-trimethylundecan-4-one

A mixture of 0.317 g. (1 mmole) of rac.-1-benzyloxy-2,6,10-trimethyl-9-undecen-4-one and 0.155 g. of 5% palladium on carbon in 20 ml. of ethyl acetate was stirred in an atmosphere of hydrogen until gas uptake ceased. Approximately 2 mmoles of hydrogen was absorbed. The catalyst was filtered and washed with ethyl acetate then the filtrate and washes were combined and concentrated under reduced pressure. The residue (0.21 g.) was chromatographed on 10 g. of silica gel. Elution with ether afforded 0.16 g. (70.6%) of rac.-1-hydroxy-2,6,10-trimethylundecan-4-one as a colorless oil.

EXAMPLE 25

Rac.2,6,10-Trimethylundecan-1-ol

Reduction of the rac.-1-hydroxy-2,6,10-trimethylundecan-4-one was carried out using the procedure described in Example 7. The rac. 2,6,10-trimethylundecan-1-ol was obtained in 64.6% yield as a colorless liquid, b.p. 87°–93° C. (bath temperature) (0.3 mm Hg.).

EXAMPLE 26 rac.-1-Benzyloxy-2,6,10-trimethylundecan-4-ol

This compound was prepared by reaction of racemic dihydrocitronellal with the Grignard reagent from rac.-3-benzyloxy-2-methyl-1-propyl bromide using the procedure described in Example 4. The carbinol mixture rac.-1-benzyloxy-2,6,10-trimethylundecan-4-ol was obtained in 66.8% yield as a pale-yellow oil, b.p. 125°–130° C. (bath temperature) (0.05 mm Hg).

EXAMPLE 27 rac.-1-Benzyloxy-2,6,10-trimethylundecan-4-one

Oxidation of rac.-1-benzyloxy-2,6,10-trimethylundecan-4-ol was carried out using the procedure described in Example 5 giving rac.-1-benzyloxy-2,6,10-trimethylundecan-4-one in 81% yield as a colorless oil, b.p. 100°–104° C. (bath temperature) (0.03 mm Hg.).

EXAMPLE 28 rac.-3-Benzyloxy-2-methyl-1-bromopropane

A solution of 39 g. (0.216 mole) of rac. 3-benzyloxy-2-methyl-1-propanol and 56.7 g. (0.216 mole) of triphenylphosphine in 216 ml. of dry dimethylformamide was stirred while 11.7 ml. (34.4 g.; 0.216 mole) of bromine was added dropwise, over a 15 minute period, keeping the temperature below 55° C. A few additional drops of bromine were added until a yellow color persisted. After cooling to 30° C., the reaction mixture was poured into water and hexane was added. The precipitated triphenylphosphine oxide was filtered and washed with hexane. The filtrate and washes were combined and separated into aqueous and organic phases. The aqueous phase was extracted once with hexane then the hexane solutions were combined, washed with 10% by weight aqueous NaHSO$_3$ and brine and dried. The organic solution was filtered and concentrated in vacuo giving 44.2 g. of residue which was distilled under high vacuum. There was obtained 42.3 g. of crude bromide as a colorless liquid, b.p. 73°–86° C. (0.05–0.1 mm Hg.). This material was dissolved in benzene and absorbed on 500 g. of silica gel. Elution with 5.2 l. of benzene gave, after solvent removal, 38 g. of residue. This material was distilled yielding 37.1 g. (70.7%) of rac.-3-benzyloxy-2-methyl-1-bromopropane as a colorless liquid, b.p. 75°–85° C. (0.05–0.1 mm Hg.).

EXAMPLE 29 rac.-3-Benzyloxy-2-methylpropionic acid

A solution of 3.2 g. (0.0154 mole) of rac.-methyl 3-benzyloxy-2-methylpropionate in 35 ml. of methanol was stirred at 0° C. while 15.4 ml. of 1 N aqueous NaOH was added dropwise. The reaction mixture was stirred at 0° C. for 1 hour then at room temperature for 2 hours. An additional 1.5 ml. of 1 N aqueous NaOH was then added and stirring was continued for 1.5 hour at room temperature. The resulting solution was diluted with water, some NaCl was added and the mixture was extracted with ether. The aqueous solution was acidified with 3 N aqueous HCl and the liberated acid was isolated by ether extraction in the usual manner giving 2.5 g. (84%) of rac.-3-benzyloxy-2-methylpropionic acid as an oil.

EXAMPLE 30 rac.-3-Hydroxy-2-methylpropionic acid

A mixture of 2 g. (0.0103 mole) of rac.-3-benzyloxy-2-methylpropionic acid, 0.5 g. of 5% palladium on carbon and 20 ml. of anhydrous tetrahydrofuran was stirred in atmosphere of hydrogen until 1 mole equivalent of hydrogen was taken up. The catalyst was filtered and washed with CH$_2$Cl$_2$ then the filtrate and washes were combined and concentrated under reduced pressure. The residue was evaporatively distilled giving 0.88 g. (82%) of rac.-3-hydroxy-2-methylpropionic acid as a viscous, colorless oil, b.p. 105°–110° C. (bath temperature) (0.275 mm Hg.).

EXAMPLE 31 rac. Methyl 3-hydroxy-2-methylpropionate

A solution of 5 g. (0.024 mole) of rac.-methyl-3-benzyloxy-2-methylpropionate in 50 ml. of ethyl acetate was treated with 0.5 g. of 5% by weight palladium on 95% by weight carbon and stirred in an atmosphere of hydrogen. When hydrogen uptake ceased, the catalyst was filtered and washed with ethyl acetate then the filtrate and washes were combined and concentrated under reduced pressure. The residue was evaporatively distilled giving 2.1 g. of rac. methyl 3-hydroxy-2-methylpropionate as a colorless liquid, b.p. 74°–78° C. (bath temperature) (11 mm Hg.).

EXAMPLE 32 rac.-tert. Butyl 3-tert. butoxy-2-methylpropionate

Treatment of rac.-3-hydroxy-2-methylpropionic acid with isobutylene using the procedure of Example 1 gave rac.-tert.butyl 3-tert. butoxy-2-methylpropionate in 81.2% yield as a colorless liquid, b.p. 81°–87° C. (bath temperature) (10 mm Hg.).

EXAMPLE 33 rac.-Methyl 3-tert. butoxy-2-methylpropionate

Treatment of rac. methyl-3-hydroxy-2-methylpropionate with isobutylene using the procedure described in Example 1 gave rac.-methyl 3-tert. butoxy-2-methylpropionate in 43.5% yield as a colorless liquid, b.p. 75°–85° C. (bath temperature) (11 mm Hg.).

EXAMPLE 34 rac.-3-tert. Butoxy-2-methyl-1-propanol

Reduction of rac.-tert. butyl 3-tert.butoxy-2-methylpropionate was carried out with lithium aluminum hydride using the procedure described in Example 2. The resulting rac.-3-tert. butoxy-2-methyl-1-propanol was obtained in 88% yield as a colorless liquid, b.p. 70°–72° C. (10 mm Hg.).

EXAMPLE 35 rac.-3-tert. Butoxy-2-methyl-1-propanol

Reduction of rac.-methyl 3-tert. butoxy-2-methylpropionate was carried out with lithium aluminum hydride using the procedure described in Example 2. The hydroxy ether rac.-3-tert. butoxy-2-methyl-1-propanol was obtained in 94.2% yield as a colorless liquid, b.p. 70°–80° C. (bath temperature (10 mm Hg.).

EXAMPLE 36 rac.-3-tert. Butoxy-2-methyl-1-bromopropane

Reaction of rac.-3-tert. butoxy-2-methyl-1-propanol with bromine-triphenylphosphine using the procedure of Example 28 gave rac.-3-tert. butoxy-2-methyl-1-bromopropane in 35% yield as a colorless liquid, b.p. 67°–77° C. (bath temperature) (9 mm Hg.).

EXAMPLE 37 rac.-1-tert. Butoxy-2,6,10-trimethylundecan-4-ol

Racemic dihydrocitronellal was reacted with the Grignard reagent derived from rac.-3-tert. butoxy-2-methyl-1-bromopropane using the procedure described in Example 4. Rac.-1-tert. butoxy-2,6,10-trimethylundecan-4-ol was obtained in 69.4% yield as a colorless oil, b.p. 75°–80° C. (bath temperature) (0.05 mm Hg.).

EXAMPLE 38 rac.-1-tert. Butoxy-2,6,10-trimethylundecan-4-one

Oxidation of rac.-1-tert. butoxy-2,6,10-trimethylundecan-4-ol was carried out using the procedure described in Example 5. Rac.-1-tert. butoxy-2,6,10-trimethylundecan-4-one was obtained in 74.4% yield as a colorless oil, b.p. 110°–115° C. (bath temperature) (0.25 mm Hg.).

EXAMPLE 39 rac.-1-Hydroxy-2,6,10-trimethylundecan-4-one

Treatment of rac.-1-tert. butoxy-2,6,10-trimethylundecan-4-one with trifluoroacetic acid followed by alkali using the procedure described in Example 6 gave rac.-1-hydroxy-2,6,10-trimethylundecan-4-one as a pale-yellow oil.

EXAMPLE 40 rac.-6-Benzyloxy-2,5,7,8-tetramethylchroman-2-ethanol-p-toluenesulfonate

Using the procedure of Example 8, rac.-6-benzyloxy-2,5,7,8-tetramethylchroman-2-ethanol was converted into rac.-6-benzyloxy-2,5,7,8-tetramethylchroman-2-ethanol p-toluenesulfonate which was obtained in essentially quantitative yield as a pale-pink glass.

EXAMPLE 41 rac.-α-Tocopheryl benzyl ether

Reaction of rac.-6-benzyloxy-2,5,7,8-tetramethylchroman-2-ethanol p-toluenesulfonate with rac.-2,6,10-trimethylundec-1-yl magnesium bromide using the procedure of Example 20 gave rac.-α-tocopheryl benzyl ether in 75.8% yield as a viscous, colorless oil.

EXAMPLE 42

(R)-(+)-4-tert. Butoxy-3-methylbutyronitrile

A mixture of 23.1 g. (0.11 mole) of bromo ether (S)-(+)-3-tert. butoxy-2-methyl-1-bromopropane and 11.07 g. (0.225 mole) of sodium cyanide in 144 ml. of methanol and 36 ml. of water was stirred and refluxed for 17 hours. After cooling, the reaction mixture was diluted with water and worked up by extraction with $CH_2Cl_2$ in the manner of Example 1. The crude product was chromatographed on 500 g. of silica gel. Elution with 9:1 parts by volume and 4:1 parts by volume hexane-ether followed by evaporative distillation gave (R)-(+)-4-tert. butoxy-3-methylbutyronitrile (11.03 g.; 64.5%) as a colorless liquid, b.p. 88°–90° C. (bath temperature) (11 mm Hg.); $[\alpha]^{25}D+7.41°$ (c 1.8, $C_6H_6$).

EXAMPLE 43

(R)-(+)-4-tert. Butoxy-3-methylbutyronitrile

A mixture of 23.1 g. (0.11 mole) of bromo ether (S)-(+)-3-tert. butoxy-2-methyl-1-bromopropane and 11.07 g. (0.225 mole) of sodium cyanide in 144 ml. of methanol and 36 ml. of water was stirred and refluxed for 17 hours. After cooling, the reaction mixture was diluted with water and worked up by extraction with $CH_2Cl_2$ in the manner of Example 1. The crude product was chromatographed on 500 g. of silica gel. Elution with 9:1 parts by volume and 4:1 parts by volume hexane-ether followed by evaporative distillation gave (R)-(+)-4-tert. butoxy-3-methylbutyronitrile (11.03 g.; 64.5%) as a colorless liquid, b.p. 88°–90° C. (bath temperature) (11 mm Hg.); $[\alpha]^{25}D+7.41°$ (c 1.8, $C_6H_6$).

EXAMPLE 44

(R)-(+)-4-tert. Butoxy-2-methylbutyronitrile

A mixture of 6.4 g. (0.021 mole) of (S)-(+)-3-tert. butoxy-2-methyl-1-propyl p-toluenesulfonate and 2.09 g. (0.043 mole) of sodium cyanide in 63 ml. of ethanol and 7 ml. of water was stirred and refluxed for 11 hours. After cooling, the reaction mixture was diluted with ice-water and worked up by extraction with $CH_2Cl_2$ in the manner of Example 1. The crude product (3.7 g.) was chromatographed on 125 g. of silica gel. Elution with 4:1 parts by volume hexane-ether gave 2.98 g. (91.7%) of R-(+)-4-tert.-butoxy-3-methylbutyronitrile as a colorless liquid.

EXAMPLE 45

(R)-4-tert. Butoxy-3-methylbutanal

A solution of 4.18 g. (0.027 mole) of (R)-(+)-4-tert. butoxy-3-methylbutyronitrile in 250 ml. of hexane was stirred and cooled to −70° C. and then treated with 19.4 ml. (0.0297 mole) of a 25% solution of diisobutylaluminum hydride in toluene, dropwise, over a 20 minute period. After the addition was complete, the reaction mixture was stirred at −70° C. for 30 minutes and then at room temperature for 4 hours before being decomposed by the addition of 2.5 ml. of ethyl acetate followed by aqueous NH$_4$Cl and finally 1 N aqueous H$_2$SO$_4$. The organic phase was separated and the aqueous phase was extracted with ether. The organic solutions were combined, washed with aqueous NaHCO$_3$ and brine then dried, filtered and concentrated under reduced pressure yielding 3.95 g. of a yellow oil. This material was evaporatively distilled giving 2.92 g. (70%) of (R)-4-tert. butoxy-3-methylbutanal as a colorless liquid, b.p. 81°–85° C. (bath temperature) (11 mm Hg.).

EXAMPLE 46

(R)-(+)-tert. Butyl 2,6-dimethyl-4-heptenyl ether

A slurry of 2.67 g. (6 mmoles) of isobutyl triphenylphosphonium iodide in 50 ml. of dry tetrahydrofuran was stirred at 0° C. while a solution of 2.94 ml. (6 mmoles) of 2.04 M n-butyllithium in hexane was added dropwise. The resulting mixture was stirred for 10 minutes and then treated with a solution of 0.475 g. (3 mmoles) of (R)-4-tert. butoxy-3-methylbutanal in 25 ml. of dry tetrahydrofuran. After the addition was complete, the reaction mixture was stirred for one hour at room temperature then treated with saturated aqueous NH$_4$Cl and worked up with hexane in the usual manner. The crude product (0.792 g.) was chromatographed on 25 g. of silica gel. Elution with 9:1 parts by volume hexane-ether followed by evaporative distillation gave 0.418 g. (70.4%) of (R)-(+)-tert. butyl-2,6-dimethyl-4-heptenyl ether as a colorless liquid, b.p. 75°–80° C. (bath temperature) (10 mm Hg.); $[\alpha]_D^{25}+11.44°$ (c 0.61, C$_6$H$_6$).

EXAMPLE 47

(R)-(+)-1-tert. Butoxy-2,6-dimethylheptane

To a stirring and refluxing slurry of 2.06 g. (0.086 mole) of magnesium powder in 5 ml. of dry tetrahydrofuran was added a crystal of iodine followed by a few drops of a solution of 10.82 g. (0.0706 moles) of 1-bromo-3-methylbutane in 35 ml. of tetrahydrofuran. After the reaction had begun, the remainder of the bromide solution was added dropwise and when the addition was complete, the mixture was stirred under reflux for one hour then cooled (Grignard solution). A solution of the (S)-(+)-3-tert. butoxy-2-methyl-1-propyl p-toluenesulfone (8.6 g.; 0.0286 mole) in 30 ml. of dry tetrahydrofuran was stirred at −70° C. while 21 ml. (0.0358 mole) of the Grignard solution was added dropwise followed by 1.47 ml. of 0.1 M dilithium tetrachlorocuprate solution in tetrahydrofuran. The resulting mixture was stirred at −70° C. for 10 minutes, at 0° C. for 2 hours and at room temperature for 18 hours then treated with 1 N aqueous H$_2$SO$_4$ and worked-up by ether extraction in the manner of Example 1. The crude oily product (8.0 g.) was chromatographed on 250 g. of silica gel. Elution with 9:1 parts by volume hexane-ether afforded 4.72 g. (82.7%) of (R)-(+)-1-tert. butoxy-2,6-dimethylheptane as a colorless liquid. A sample prepared in this way was distilled giving a colorless liquid, b.p. 94°–96° C. (20 mm Hg.); $[\alpha]^{25}D+9.91°$ (c 1.22, C$_6$H$_6$).

EXAMPLE 48

(R)-(+)-1-tert. Butoxy-2,6-dimethylheptane

A solution of 1.7 g. (8.6 mmoles) of (R)-(+)-1-tert. butyl 2,6-dimethyl-4-heptenyl ether in 100 ml. of ethyl acetate was stirred in an atmosphere of hydrogen in the presence of 0.5 g. of 5% by weight palladium on 95% by weight carbon. When hydrogen uptake ceased, the catalyst was filtered and the filtrate was concentrated in vacuo. Evaporative distillation of the residue afforded 1.45 g. (84.4%) of the (R)-(+)-1-tert. butoxy-2,6-dimethylheptane as a colorless liquid, b.p. 82°–85° C. (bath temperature) (10 mm Hg.).

EXAMPLE 49

(R)-(+)-1-tert. Butoxy-3-methylbutyric acid

A solution of 5.0 g. (0.0323 mole) of R-(+)-4-tert. butoxy-3-methylbutyronitrile in 200 ml. of 10% aqueous KOH solution was stirred and refluxed for 16 hours. The resulting mixture was cooled in an ice bath, acidified with 6 N aqueous HCl and worked up in the manner of Example 1 by ether extraction. The crude product (5.52 g.) was chromatographed on 150 g. of silica gel. Elution with 4:1 parts by volume and 2:1 parts by volume ether-hexane yielded 4.24 g. (75%) of (R)-(+)-4-tert. butoxy-3-methylbutryic acid as a colorless oil; $[\alpha]^{25}D+11.02°$ C. (c 1.997, C$_6$H$_6$).

EXAMPLE 50

(R)-(+)-4-tert. Butoxy-3-methyl-1-butanol

A slurry of 1.51 g. (0.0398 mole) of lithium aluminum hydride in 50 ml. of ether was stirred and cooled while a solution of 3.45 g. (0.0198 mole) of (R)-(+)-4-tert. butoxy-3-methylbutyric acid in 50 ml. of ether was added dropwise. After the addition was complete, the reaction mixture was stirred at room temperature for 2 hours then cooled to 0° C. and cautiously decomposed with 5.4 ml. of saturated aqueous Na$_2$SO$_4$ solution. After stirring at room temperature for 18 hours, the mixture was filtered and the filtrate was concentrated under reduced pressure. The crude product (3.05 g.) was chromatographed on 100 g. of silica gel. Elution with 2:1 parts by volume, 1:1 parts by volume and 1:2 parts by volume hexane-ether followed by evaporative distillation gave 2.68 g. (85%) of the (R)-(+)-4-tert. butoxy-3-methyl-1-butanol as a colorless liquid, b.p. 100°–102° C. (bath temperature) (20 mm Hg.); $[\alpha]^{25}D+12.79°$ (c 2.19, C$_6$H$_6$).

EXAMPLE 51

(R)-(+)-4-tert. Butoxy-3-methyl-1-butanol-p-toluenesulfonate

Using the procedure of Example 8, (R)-(+)-4-tert. butoxy-3-methyl-1-butanol was converted into (R)-(+)-4-tert. butoxy-3-methyl-1-butanol p-toluenesulfonate which was isolated in 90% yield as a pale yellow oil.

EXAMPLE 52

(R)-(+)-1-tert. Butoxy-2,6-dimethylheptane

Coupling of (R)-(+)-4-tert. butoxy-3-methyl-1-butanol p-toluenesulfonate with isobutylmagnesium bromide was carried out using the procedure of Example 47. (R)-(+)-1-tert. Butoxy-2,6-dimethylheptane was obtained in 76% yield as a colorless liquid.

EXAMPLE 53

(R)-(+)-2,6-Dimethyl-1-heptanol

Treatment of the ether (R)-(+)-1-tert. butoxy-2,6,-dimethylheptane with trifluoroacetic acid followed by alkali using the procedure described in Example 6 gave (R)-(+)-2,6-dimethyl-1-heptanol as a colorless liquid, b.p. 92°-95° C. (bath temperature) (16 mm Hg.); $[\alpha]^{25}D + 10.14°$ (c 2.01, $C_6H_6$).

EXAMPLE 54

(R)-1-Bromo-2,6-dimethylheptane

Treatment of (R)-(+)-2,6-dimethyl-1-heptanol with N-bromosuccinimidetriphenylphosphine using the procedure described in Example 10 gave (R)-1-bromo-2,6-dimethylheptane in 89% yield as a colorless liquid, b.p. 90°-92° C. (bath temperature) (20 mm Hg.); $[\alpha]^{25}D + 0.48°$ (c 5.17, $C_6H_6$).

EXAMPLE 55

(R)-(−)-3,7-Dimethyloctanenitrile

Treatment of (R)-1-bromo-2,6-dimethylheptane with sodium cyanide using the procedure of Example 42 gave (R)-(−)-3,7-dimethyloctanenitrile in 64% yield, as a colorless liquid, b.p. 106°-108° C. (bath temperature) (20 mm Hg.); $[\alpha]^{25}D - 3.51°$ C. (c 2.08, $C_6H_6$).

EXAMPLE 56

R-(+)-Dihydrocitronellic acid

A solution of 3.35 g. (0.0234 mole) of (R)-(−)-3,7-dimethyloctanenitrile and 10 g. (0.179 mole) of KOH in 90 ml. of 90% by weight aqueous ethylene glycol was refluxed and stirred for three hours. After cooling, the reaction mixture was acidified with 3 N aqueous HCl and worked up in the manner of Example 1 by ether extraction giving 3.95 g. of yellow oily product. A 3.1 g. sample of this material was chromatographed on 100 g. of silica gel. Elution with 9:1 parts by volume, 4:1 parts by volume and 2:1 parts by volume hexane-ether followed by evaporative distillation yielded 2.53 g. of R-(+)-dihydrocitronellic acid, b.p. 88°-91° C. (bath temperature) (0.25 mm Hg.); $[\alpha]^{25}D + 7.25°$ C. (c 5, $CHCl_3$).

EXAMPLE 57

Rac. 3-benzyloxy-2-methyl-1-propanol

A solution of 1.59 g. of sodium hydroxide and 1.6 ml. of water in 402 ml. (420 g; 3.89 moles) of benzyl alcohol was stirred and cooled to −10° C. while 100 ml. (83.7 g.; 1.19 moles) of freshly distilled methacrolein were added dropwise keeping the temperature between −10° C. and −5° C. After the reaction mixture had stirred for 0.5 hr. at −10° C., a solution of 44.9 g. (1.19 moles) of sodium borohydride in 180 ml. of water was added dropwise over 1.75 hr. keeping the temperature below 5° C. Stirring was continued for an additional hour during which time the reaction mixture was allowed to warm to room temperature. The resulting mixture was poured into ice-water and the organic materials were extracted several times with ether. The ether extracts were worked up by first combining the extracts washing with saturated brine and drying over anhydrous magnesium sulfate. After filtration and removal of the solvents in vacuo, the residue was carefully fractionated, giving, after removal of low boiling materials, 39.6 g. of rac. 3-benzyloxy-2-methyl-1-propanol as a colorless liquid, b.p. 91°-98° C. (0.5 mm Hg.).

EXAMPLE 58

(2R,6R)-(+)-1-tert. Butoxy-2,6,10-trimethylundecane

Reaction of the Grignard reagent, i.e., the magnesium salt of (R)-1-bromo-2,6-dimethylheptane with the (R)-(+)-4-tert. butoxy-3-methyl-1-butanol p-toluenesulfonate was carried out using the procedure described in Example 12. The desired product (2R,6R)-(+)-1-tert. butoxy-2,6,10-trimethylundecane was obtained as a colorless oil, b.p. 90° C. (bath temperature) (0.1 mm Hg.).

EXAMPLE 59

2S, βR)-6-Benzyloxy-2,5,7,8 β-pentamethylchroman-2-pentanol

A solution of the Grignard reagent, i.e., the magnesium salt of (S)-(+)-3-tert. butoxy-2-methyl-1-bromopropane in THF (12 ml.) was prepared from 1.47 g. (7.05 mmoles) of the (S)-(+)-3-tert. butoxy-2-methyl-1-bromopropane in Example 4. This solution was then added, dropwise, to a stirred solution of 2.90 g. (5.87 mmoles) of (S)-(+)-6-Benzyloxy-2,5,7,8-tetramethylchroman-2-ethanol p-toluenesulfonate in 5 ml. of dry THF, with cooling from a dry ice-acetone bath. After the addition of 0.25 ml. of 0.1 N dilithium tetrachlorocuprate solution in THF, the reaction mixture was stirred at −72° C. for 10 minutes, for 2 hours at 0° C. and for 19 hours at room temperature. The reaction mixture was then poured into 25 ml. of 1 N aqueous $H_2SO_4$ and the organic materials were extracted three times with ether. The combined ether extracts were washed with water and brine and dried. Filtration and solvent removal gave 3.1 g. of crude product which was chromatographed on 250 g. of silica gel. Elution with 9:1 hexane-ether gave the desired coupling product the tertiary butyl ether of (2S, βR)-6-benzyloxy-2,5,7,8 β-pentamethylchroman-2-pentanol as a viscous oil which solidified on storage.

A mixture of 1.05 g. (2.32 mmoles) of the tertiary butyl ether of (2S, βR)-6-Benzyloxy-2,5,7,8 β-pentamethylchroman-2-pentanol and 220 mg. of p-toluenesulfonic acid monohydrate in 45 ml. of benzene was stirred and refluxed for 5.5 hours. After cooling, the benzene solution was washed with saturated aqueous $NaHCO_3$ and brine and dried. Filtration and solvent removal afforded 0.939 g. of a viscous oil. This material was chromatographed on 50 g. of silica gel. Elution with 1:1 parts by volume of hexane/ether and ether gave 0.595 g. (64.8%) of the (2S, βR)-6-Benzyloxy-2,5,7,8 β-pentamethylchroman-2-pentanol as a viscous, colorless oil; $[\alpha]^{25} D + 3.68°$.

EXAMPLE 60

(2S, βR)-6-Benzyloxy-2,5,7,8 β-pentamethylchroman-2-pentanol-p-toluenesulfonate A solution of 0.73 g. (1.84 mmoles) of (2S,βR)-6-Benzyloxy-2,5,7,8, β-pentamethylchroman-2-pentanol and 0.704 g. (3.68 mmoles) of p-toluenesulfonyl chloride in 12.5 ml. of dry pyridine was kept for 20 hours at 0° C. then treated with ice water. The organic materials were extracted three times with ether and the combined ether extracts were washed with 1 N aqueous HCl and brine and dried. Filtration and solvent removal gave 1.04 g. of the (2S,βR)-6-Benzyloxy-2,5,7,8 β-pentamethylchroman-2-pentanol p-toluenesulfonate as a yellow oil.

EXAMPLE 61

(2S,4'S,8'S)-α-Tocopherol Benzyl Ether

A solution of the Grignard reagent, i.e., the magnesium salt of (R)-(−)-1-bromo-3,7-dimethyloctane in THF (8 ml.) was prepared from 0.487 g. (2.21 mmoles) of the (R)-(−)-1-bromo-3,7-dimethyloctane as in Example 4. This solution was then added, dropwise, to a stirred solution of (2S, βR)-6-Benzyloxy-2,5,7,8 β-pentamethylchroman-2-pentanol p-toluenesulfone (1.84 mmoles) in 5 ml. of dry THF, cooled to −72° C. with a dry ice-acetone bath. The reaction mixture was treated with 0.1 ml. of 0.1 N dilithium tetrachlorocuprate solution in THF and stirred for 10 minutes at −72° C., for 2 hours at 0° C. and finally for 16.5 hours at room temperature before being poured onto 25 ml. of 1 N aqueous H$_2$SO$_4$. The organic materials were extracted three times with ether then the combined ether extracts were washed with water and brine and dried. Filtration and solvent removal yielded 1.019 g. of an oil which was chromatographed on 50 g. of silica gel. Elution with 19:1 hexane-ether gave (2S,4'S,8'S)-α-tocopherol benzyl ether (0.277 g.) which was further purified by preparative thin layer chromatography (silica gel-19:1 parts by volume hexane-ether). There was obtained 0.124 g. (11.9%) of pure (2S,4'S,8'S)-α-tocopherol benzyl ether as a viscous, pale-yellow oil; $[\alpha]_D^{25}$ −0.69° (c 2.46, C$_6$H$_6$).

We claim:

1. A compound of the formula:

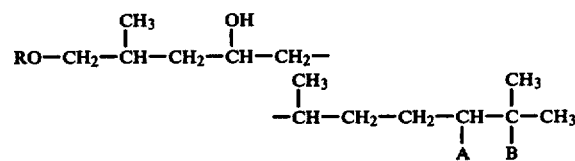

where R is tetrahydropyranyl, 4-methyl-5,6-dihydro-2H-pyranyl, arylmethyl, alpha-lower alkoxy-lower alkyl, tri(loweralkyl)silyl, or t-butyl; A and B are individually hydrogen or taken together form a carbon to carbon bond.

2. The compound of claim 1 wherein said compound is rac.-1-benzyloxy-2,6,10-trimethyl-9-undecen-4-ol.

3. The compound of claim 1 wherein said compound is a mixture of (2R,4R,6R)- and (2R,4S,6R)-1-tert. butoxy-2,6,10-trimethylundecan-4-ol.

* * * * *